United States Patent [19]

Sone et al.

[11] 4,166,128
[45] Aug. 28, 1979

[54] SUBSTITUTED PHENYLGLYCOLIC ACID AND ITS PHARMACEUTICALLY ACCEPTABLE ESTERS AND SALTS, AND PROCESSES FOR PREPARING THE SAME

[75] Inventors: Takanori Sone; Shinichi Furukawa; Mikio Wakabayashi; Ryoji Kodaira, all of Nobeoka, Japan

[73] Assignee: Asahi Kasei Kogyo Kabushiki Kaisha, Osaka, Japan

[21] Appl. No.: 851,637

[22] Filed: Nov. 15, 1977

[30] Foreign Application Priority Data

Jun. 23, 1977 [JP] Japan .................................. 52/74722

[51] Int. Cl.$^2$ ....................... A01N 9/20; C07C 101/72
[52] U.S. Cl. .................................... 424/319; 560/45; 562/454; 424/309
[58] Field of Search .......................... 260/518 R, 519; 424/319, 309; 562/454; 560/45

[56] References Cited

U.S. PATENT DOCUMENTS

| 3,558,690 | 1/1971 | Sallmann et al. | 260/519 |
| 3,652,762 | 3/1972 | Sallmann et al. | 260/519 |
| 3,681,394 | 8/1972 | Sherlock | 260/519 |
| 3,766,260 | 10/1973 | Carney et al. | 260/519 |
| 3,778,470 | 12/1973 | Sallmann et al. | 260/519 |

FOREIGN PATENT DOCUMENTS 1815802 7/1969 Fed. Rep. of Germany ........... 562/454

*Primary Examiner*—James H. Reamer
*Attorney, Agent, or Firm*—Armstrong, Nikaido, Marmelstein & Kubovcik

[57] ABSTRACT

Novel substituted phenylglycolic acid represented by the formula

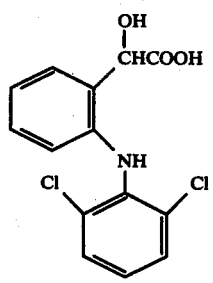

and its pharmaceutically acceptable non-toxic esters and salts have potent analgesic, anti-inflammatory and antipyretic activities, a low toxicity and a satisfactory therapeutic index, and can be favorably employed as a medicine for treatment of various inflammatory diseases such as arthritis, common cold, rheumatism and like inflammations and also for analgesic and antipyretic purposes. The substituted phenylglycolic acid is prepared by reacting a lower alkyl ester of 2-(2,6-dichloroanilino)phenylglycolic acid with a basic substance, which lower alkyl ester is also a novel compound and can be obtained starting from 1-(2,6-dichlorophenyl)indole-2,3-dione through 2-(2,6-dichloroanilino)phenylglyoxylic acid and, in turn, a lower alkyl ester of 2-(2,6-dichloroanilino)-phenylglyoxylic acid.

9 Claims, 3 Drawing Figures

SUBSTITUTED PHENYLGLYCOLIC ACID AND ITS PHARMACEUTICALLY ACCEPTABLE ESTERS AND SALTS, AND PROCESSES FOR PREPARING THE SAME

This invention relates to a novel substituted phenylglycolic acid and pharmaceutically acceptable esters and salts thereof, an analgesic, anti-inflammatory and antipyretic composition containing at least one of these compounds and a chemical process for preparing these compounds.

More particularly, the present invention is concerned with a substituted phenylglycolic acid having the formula 1 and pharmaceutically acceptable esters and salts thereof; an analgesic, anti-inflammatory and antipyretic composition which comprises as an active ingredient at least one of a substituted phenylglycolic acid (I) and pharmaceutically accetable esters and salts thereof; and a chemical process for preparing these compounds.

There are not known a substituted phenylglycolic acid represented by the formula (I) and pharmaceutically acceptable esters and salts thereof.

The present inventors have made earnest studies and found that a substituted phenylglycolic acid (I) and pharmaceutically acceptable esters and salts thereof exhibit remarkably high pharmacological activities, especially analgesic, anti-inflammatory and antipyretic activities, and are useful as a medicine.

It is, accordingly, an object of this invention to provide a new class of substituted phenylglycolic acid (I) and pharmaceutically acceptable esters and salts thereof which have effective analgesic, anti-inflammatory and antipyretic activities, a low toxicity and a satisfactory therapeutic effect.

Another object of this invention is to provide a simple and advantageous process for preparing a new and useful substituted phenylglycolic acid (I) and pharmaceutically acceptable esters and salts thereof.

Still another object of this invention is to provide a pharmaceutical composition which comprises as an active ingredient at least one of a substituted phenylglycolic acid (I) and pharmaceutically acceptable esters and salts thereof.

In one aspect of this invention, there is provided a substituted phenylglycolic acid (I), or its pharmaceutically acceptable ester or salt. They have been found to have potent analgesic, anti-inflammatory and antipyretic activities, a low toxicity and a satisfactory therapeutic index. Therefore, the substituted phenylglycolic acid (I) and pharmaceutically acceptable esters and salts of this invention can be favourably employed as a medicine for treatment of various inflammatory diseases such as arthritis, common cold, rheumatism and like inflammations and also for analgesic and antipyretic purposes. The substituted phenylglycolic acid (I) of this invention and its pharmaceutically acceptable esters and salts can be administered orally or parenterally, preferably via oral route, according to conventional procedures, for instance, in the form of tablets, capsules, powders, granules, fine granules, injectable liquids and the like. The dosage may vary depending upon ages, severities and body weights of patients, but a substituted phenylglycolic acid (I), ester or salt may be usually administered in a daily dose of from about 500 mg to about 1.2 g for adults, if necessary, in divided dosage forms.

Examples of the pharmaceutically acceptable esters of a substituted phenyglycolic acid of the formula (I) include lower alkyl esters of the acid. Such lower alkyl esters of 2-(2,6-dichloroanilino)phenylglycolic acid may include those esters having as an alkyl moiety a straight or branched lower alkyl group of 1 to 8 carbon atoms, for example, methyl, ethyl, n-propyl, isopropyl, n-butyl, tert-butyl, n-pentyl, isopentyl, hexyl, heptyl, octyl, etc. In view of a pharmacological activity, there may be preferably mentioned the methyl ester and the ethyl ester.

The pharmaceutically acceptable salts of 2-(2,6-dichloroanilino)phenylglycolic acid (I) according to this invention include, for example, those alkali metal salts such as sodium or potassium salt; those alkaline earth metal salts such as calcium or barium salt; aluminum salt; ammonium salt; as well as those salts with organic bases such as dialkylamines, e.g., mono or diethylamine, alkanolamines, e.g., ethanolamine, heterocyclic amines, e.g., pyridine, piperidine, piperazine, morpholine and the like. In view of practical application, there may be preferably mentioned the alkali metal salts, particularly sodium salt of the acid (I).

In order to demonstrate potent analgesic, anti-inflammatory and antipyretic activities and low toxicities of a substituted phenylglycolic acid of the formula (I) and esters and salts thereof, there are given hereinbelow some experimental data for illustrative purpose only.

I. Anti-inflammatory Activity

(1) Carrageenin Edema Test in Rats

Male Wistar-strain rats weighing about 120 g, each group consisting of 10 animals, were fasted overnight and then orally given the test drug. After 1 hour from the oral administration, inflammation was introduced by injection of 0.1 ml of 1% carrageenin suspension into the plantar tissue of rat's right hind paw subcutaneously. Paw edema was measured volumetrically every hour over 5 hours after the carrageenin injection and edema percent and inhibition percent were determined.

(2) UV-erythema Test in Guinea Pigs

Hartley-strain guinea pigs weighing about 200 g were employed and test was conducted according to the method reported by Winder et al. in Arch. int. Pharmacodyn., 116, 261 (1958). Guinea pigs were depilated on ventral portion on the day before test and then applied on depilated portion with a synthetic rubber piece having 3 holes. Ultraviolet ray was irradiated on the portion for 30 seconds at a distance of 15 cm by the use of HQ-400Q photochemical mercury-arc lamp. The test drug was orally given to animals in a half amount thereof before 1 hour of the irradiation and in the remaining half amount immediately after the irradiation.

Erythema was visually determined 2 hours and 5 hours after the irradiation, according the following ratings:
1: Erythema with sharp demarcation of irradiated portion
0.5: Erythema with dull demarcation
0: Erythema scarcely observed Then, not less than 2 of the sum of three portions was evaluated as ineffective and not more than 1.5 was evaluated as effective in inhibition.

II. Analgesic Activity

(1) Acetic Acid-Stretching Test in Mice

Male ddY-strain mice weighing about 20 g, each group consisting of 20 animals, were orally given the test drug and 0.4 ml of 0.25% acetic acid as a stimulant was intraperitoneally administered after 60 minutes from the oral administration. Immediately after the stimulant administration, writhing syndrome as pain response was observed and recorded over 20 minutes.

III. Acute Toxicity

Acute toxicity ($LD_{50}$) was determined by oral administration to male Wistar-strain rats weighing about 120 g of the test drug and observation for 9 days, each group consisting of 10 animals.

The results of these tests are summarized as seen below.

I. Anti-inflammatory Activity

(1) Carrageenin Edema Test

Figure 1:
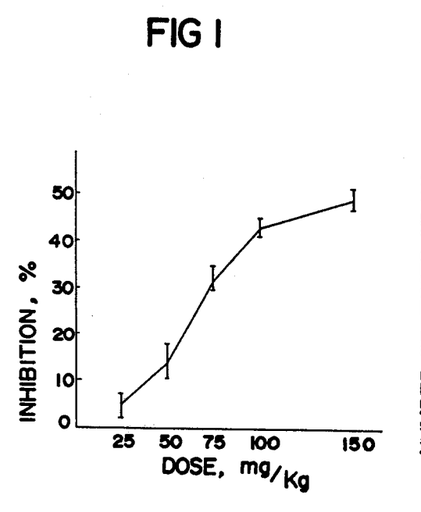
Figure 2:
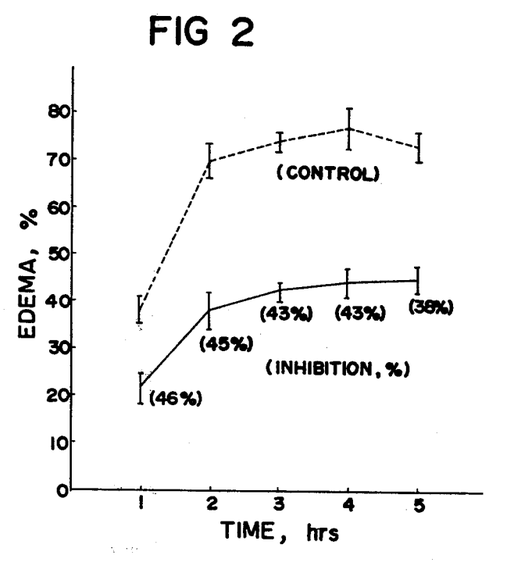

When sodium 2-(2,6-dichloroanilino)phenylglycolate was employed as the test drug, a potent activity was observed with at least 50 mg/kg and extremely high inhibition percents of 43% with 100 mg/kg and of 49% with 150 mg/kg were seen as shown in FIGS. 1 and 2. In FIG. 1, there are shown inhibition percents observed 3 hours after the injection of carrageenin suspension. In FIG. 2, there are shown edema percents and inhibition percents observed with administration of 100 mg/kg of the test drug, together with the curve of control.

When methyl 2-(2,6-dichloroanilino)phenylglycolate was employed, a potent activity was observed with at least 50 mg/kg, and inhibition percent of about 30% was seen with 100 mg/kg.

(2) UV-erythema Test

When sodium 2-(2,6-dichloroanilino)phenylglycolate was employed, the results are shown in Table.

Table

| Dose (mg/kg) | 25 | | 50 | | 100 | |
| --- | --- | --- | --- | --- | --- | --- |
| Time (hrs.) | 2 | 5 | 2 | 5 | 2 | 5 |
| Effective/Total | 4/6 | 2/6 | 6/6 | 3/6 | 6/6 | 4/6 |
| Effectiveness (%) | 67 | 33 | 100 | 50 | 100 | 67 |

II. Analgesic Activity

Figure 3:
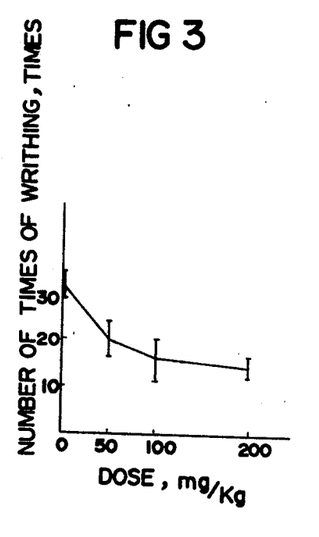

Effectivenesses of 50% with 100 mg/kg and 56% with 200 mg/kg were observed as seen in FIG. 3. The test drug was sodium 2-(2,6-dichloroanilino)phenylglycolate.

III. Acute Toxicity $LD_{50}$ of sodium 2-(2,6-dichloroanilino)phenylglycolate was 675–730 mg/kg.

It can be fairly concluded from the results that the present acid (I), and esters and salts thereof are usable as very safe and effective analgesic, anti-inflammatory and antipyretic drugs.

In another aspect of this invention, there are provided processes for preparing a substituted phenylglycolic acid represented by the formula (I), and pharmaceutically acceptable esters and salts thereof.

Essentially, a substituted phenylglycolic acid of the formula (I), namely 2-(2,6-dichloroanilino)phenylglycolic acid is prepared by reacting a lower alkyl ester of 2-(2,6-dichloroanilino)phenylglycolic acid represented by the formula (III)

wherein R is a lower alkyl group with a basic substance. The lower alkyl ester of 2-(2,6-dichloroanilino)phenylglycolic acid is also a novel compound and one class of the desired compounds of the present invention, and can be obtained starting from 1-(2,6-dichlorophenyl)-indole-2,3-dione through 2-(2,6-dichloroanilino)phenylglyoxylic acid and, in turn, a lower alkyl ester of 2-(2,6-dichloroanilino)phenylglyoxylic acid.

Accordingly, as a whole process for the preparation of 2-(2,6-dichloroanilino)phenylglycolic acid of the formula (I), there can be mentioned a process which comprises the steps of:

(1) treating 1-(2,6-dichlorophenyl)indole-2,3-dione with a basic substance;

(2) reacting the reaction product in the step (2) with an alkylating agent in an inert solvent under neutral or alkaline condition to produce a lower alkyl ester of 2-(2,6-dichloroanilino)phenylglyoxylic acid having the formula wherein R is a lower alkyl group;

(3) subjecting the ester (II) to a treatment with a hydride reagent or to a catalytic reduction to produce a lower alkyl ester of 2-(2,6-dichloroanilino)phenylglycolic acid having the formula (III)

wherein R is as defined above; and (4) reacting the ester (III) with a basic substance to produce the salt, corresponding to the basic substance, of 2-(2,6-dichloroanilino)phenylglycolic acid of the formula (I), followed by a treatment of said salt with a mineral acid.

In carrying out the process of this invention, the step (1) may preferably be effected in the presence of a solvent. As the solvent, there may be employed a mixture of water with any water-miscible organic solvent that does not participate in the reaction. Preferred example of such organic solvent is a lower alkanol such as methanol, ethanol or the like. As the basic substance which may be employed in this step (1), namely the hydrolysis step, there may be mentioned, for example, an alkali metal hydroxide, an alkaline earth metal hydroxide, an alkali metal carbonate, an alkali metal hydrogen carbonate and the like. The basic substance is usually and advantageously employed in an amount of 1 to 10 equivalents, preferably 1 to 3 equivalents, more preferably 1 to 1.2 equivalents to the starting material. Reaction temperature is not particularly critical, but the reaction may be usually effected at a temperature 0° to 80° C., preferably around room temperature. Reaction period of time may vary depending mainly upon the reaction temperature employed and may usually be in the range of 5 minutes to 10 hours, preferably 20 minutes to 1 hour, but there is also no particular limitation. After completion of the hydrolysis, the reaction product is present in situ in the form of the corresponding metal salt of 2-(2,6-dichloroanilino)phenylglyoxylic acid, and may be isolated as such by a conventional method. If desired, the so obtained metal salt may be isolated in the form of the free acid, namely 2-(2,6-dichloroanilino)phenylglyoxylic acid, by the treatment with a suitable acid. Either the metal salt or the free acid may be employed for the subsequent step (2). From view points of ease of the reaction conditions and improved yields in the step (2), the reaction product in the step (1) may advantageously be isolated in the form of the free acid and employed for the step (2).

In order to isolate the reaction product in the step (1) in the form of the free acid, there may be employed a method in which, after completion of the reaction, the solvent is distilled off, the residue is dissolved in water, the pH of the resulting solution is adjusted to about 2 to 3 by adding thereto a suitable acid, whereupon the crystals deposited are separated by filtration or extracted with a suitable organic solvent. The suitable acids to be employed may be mineral acids such as hydrochloric acid, sulfuric acid, phosphoric acid and the like. Hydrochloric acid is particularly preferred. The suitable organic solvents to be employed may be those solvents that are water-immiscible and capable of well dissolving the free acid. Such organic solvents include, for example, dichloromethane, chloroform, ether, benzene, ethyl acetate and the like. Dichloromethane, chloroform and ether are particularly preferred.

The step (2) of the present process, namely, alkylation of the glyoxylic acid produced in the step (1) should be conducted under neutral or alkaline condition, since intramolecular ring closure tends to preferentially occur under acidic condition, which is not desirable and to be avoided.

One mode of the alkylation process in the step (2) may comprise treating the metal salt of 2-(2,6-dichloroanilino)-phenylglyoxylic acid produced in the step (1), as such or in the form of the free acid, with an alkylating agent such as a di(lower)alkyl sulfate, e.g., dimethyl sulfate or diethyl sulfate or a lower alkyl halide, e.g., methyl iodide or ethyl bromide, in the presence of a basic substance, for example, an alkali metal hydroxide, an alkali metal carbonate, an alkali metal hydrogen carbonate or an alkali metal acetate and in the presence of an inert solvent such as acetone or dimethylformamide under anhydrous condition. In this mode of alkylation process, there is no particular limitation upon the amount of the alkylating agent employed, but the agent is usually and preferably employed in an amount of 1 to 5 equivalents, preferably 1 to 2 equivalents to the starting acid or salt. The basic substance, e.g., an alkali metal hydroxide, an alkali metal carbonate, an alkali metal hydrogen carbonate or an alkali metal acetate is used for providing the alkaline condition in the alkylation process, and the amount thereof may be in the range of 1 to 5 moles, preferably 2 to 3 moles per mole of the starting acid or salt. Reaction temperature is not particularly critical, but there may usually be employed temperatures of −20° to 50° C., preferably 0° to 20° C. Generally, the reaction may proceed rapidly under such a mild temperature condition as, for example, around room temperature or ice-cooling, and hence, heating is not needed. Reaction time is also not particularly critical, but there may usually be employed 30 minutes to 10 hours, preferably 1 to 3 hours.

Alternatively, there may be employed another mode of the alkylation process in the step (2) comprising treating the reaction product produced in the step (1), in the form of the free acid, with a diazoalkane as an alkylating agent, e.g., diazomethane in an inert solvent such as ether. In the alternative mode of alkylation process, there is no particular limitation upon the amount of a diazoalkane employed as the alkylating agent, but the agent is usually and preferably employed in an amount of 1 to 5 moles, preferably 1 to 2 moles per mole of the starting acid. Reaction temperature is not particularly critical, but there may usually be employed temperatures of −20° to 30° C., preferably −10° to 20° C.

In any of the two modes of the alkylation process in the step (2), the desired 2-(2,6-dichloroanilino)phenylglyoxylic acid ester of the formula (II) is obtained in high yield, almost quantitatively. After completion of the alkylation reaction in the step (2), the desired ester (II) may be recovered from the reaction mixture by a customary method. For instance, when the dialkyl sulfate or alkyl halide is employed as the alkylating agent, insoluble substances are removed by filtration and the filtrate is concentrated, whereupon the residue is recrystallized from a suitable solvent or is subjected to a column chromatography using, e.g., silica gel to give the pure desired ester (II). When the diazoalkane is employed as the alkylating agent, the diazoalkane remaining after completion of the reaction is decomposed with a suitable aqueous weak acid solution, an organic layer is separated and concentrated and then the residue is recrystallized from a suitable solvent to give the pure desired ester (II).

The step (3) of the present process, namely, reduction of the ester (II) produced as above to the 2-(2,6-dichloroanilino)phenylglycolic acid ester (III) may be conducted in two alternative reduction procedures. One reduction procedure is reduction with a hydride reagent and another one is catalytic reduction with a hydrogen gas.

In the former reduction, there may be employed as the reagent, for example, sodium borohydride, sodium bis(2-methoxyethoxy)aluminum hydride, lithium tri-tert-butoxy aluminum hydride and the like and sodium borohydride is particularly preferred. When sodium borohydride is employed, the solvent to be used may preferably be a lower alkanol such as methanol, ethanol and the like. An amount of the reagent may be in the range of 1 to two equivalents, preferably 1 to 1.1 equivalent to the starting ester (II). Reaction temperature is usually $-30°$ to $50°$ C., preferably $-20°$ to $20°$ C. Reaction period of time is usually 30 minutes to 7 hours, preferably 1 to 2 hours.

In conducting the latter reduction, i.e., catalytic reduction, there may be used as a noble metal catalyst various forms of palladium catalysts or platinum catalysts. As the palladium catalyst, there may be preferably employed, for example, palladium-carbon, palladium-barium sulfate, palladium black and the like. As the platinum catalyst, there may be preferably employed, for example, platinum-carbon, platinum oxide, platinum black and the like. Palladium-carbon and platinum-carbon are particularly preferred. An amount of the catalyst to be used may be in the range of 1 to 30% by weight, preferably 5 to 10% by weight based on the starting ester (II). A reaction solvent is significant in this catalytic reduction and a lower alkanol may preferably be employed for obtaining the desired glycolic acid ester (III) with high selectivity. Particularly, methanol and ethanol are preferable. The lower alkanol may be employed alone, or may more advantageously be used together with a minor amount of an aliphatic carboxylic acid especially when the reaction is slower. As the aliphatic carboxylic acid, there may be recited, for example, acetic acid, propionic acid and the like. Of these aliphatic carboxylic acids, acetic acid is particularly preferred. An amount of the aliphatic carboxylic acid when employed with the alkanol may preferably be of such an order that an about 0.1 to 1.0 N solution of the acid in the alkanol can be formed. The reaction can proceed rapidly at around $50°$ C. so that heating at a temperature higher than $50°$ C. is not usually required. Generally, however, there may be employed temperatures of $0°$ to $100°$ C., preferably room temperature to $50°$ C. Hydrogen pressure to be applied may be 1 to 10 atm., preferably 1 to 5 atm. Reaction period of time may be in the range of 30 minutes to 5 hours, preferably 1 to 3 hours.

After completion of the reduction, the desired glycolic acid ester (III) may be recovered by a customary method. For instance, when the hydride reagent was employed in the step (3), the remaining reagent is decomposed with a suitable acid or, when the catalyst was employed in the step (3), it is filtered off. Subsequently, the reaction mixture thus treated is washed with water and extracted with a suitable organic solvent, the solvent is distilled off and then the residue is recrystallized from, e.g., ethanol to give a lower alkyl ester of 2(2,6-dichloroanilino)phenylglycolic acid of the formula (III) in the purified form. As aforementioned, the lower alkyl ester (III) thus obtained is one class of the desired compounds according to the present invention, and the ester (III) as such may be utilized for the pharmaceutical purposes.

According to the whole process for the preparation of a substituted phenylglycolic acid of the formula (I), the lower alkyl ester (III) obtained in the step (3) is subjected to a treatment in the subsequent step (4).

In the step (4) of the process of the present invention, the ester (III) is reacted with a basic substance, usually in the presence of a reaction medium. As the reaction medium, there may be employed a mixture of water with a water-miscible organic solvent that does not participate in the reaction. A typical example of the reaction solvent is a mixture of water with a lower alkanol such as methanol, ethanol or the like. Examples of the basic substance which may be employed include an alkali metal hydroxide, an alkaline earth metal hydroxide, an alkali metal carbonate, an alkaline ion exchanger and the like, and the basic substance may be employed in an amount of 1 to 10 equivalents, preferably 1 to 1.5 equivalents to the starting ester (III). Reaction temperature is not critical, but the reaction may be conducted at $-20°$ to $150°$ C., preferably $0°$ to $80°$ C. The reaction may smoothly proceed around room temperature. Reaction period of time may usually be in the range of 10 minutes to 2 hours, preferably 30 minutes to 1 hour, but there is also no particular limitation. After completion of the reaction, the reaction product is present in situ in the form of the corresponding metal salt of 2-(2,6-dichloroanilino)phenylglycolic acid.

In order to isolate the metal salt as such, the reaction mixture is cooled to about $0°$ to $10°$ C. to deposit the desired metal salt as crystals. The metal salt thus obtained is also one class of the desired compounds of the present invention, and the metal salt as such may be utilized for the phamaceutical purposes.

According to the process of the present invention, the metal salt thus obtained is further treated to isolate, as the free acid, 2-(2,6-dichloroanilino)phenylglycolic acid of the formula (I). In order to isolate the reation product in the step (4) in the form of the free acid, there may be employed a method in which, after completion of the reaction, the solvent is distilled off, the residue is dissolved in water, the pH of the resulting solution is adjusted to about 2 to 3 by adding thereto a suitable acid, whereupon the crystals deposited are separated by filtration or extracted with a suitable organic solvent. The suitable acids to be employed may be mineral acids such as hydrochloric acid, sulfuric acid, phosphoric acid and the like. Hydrochloric acid is particularly preferred. The suitable organic solvents to be employed may be those solvents that are water-immiscible and capable of well dissolving the free acid. Such organic solvents include, for example, ether, benzene, toluene, dichloromethane, chloroform, carbon tetrachloride and the like. Ether, dichloromethane and chloroform are particularly preferred.

The 2-(2,6-dichloroanilino)phenylglycolic acid thus obtained in the form of a free acid may, if desired, be further treated according to a customary method, so that other salts of the substituted phenylglycolic acid (I) than alkali metal salts and alkaline earth metal salts, namely aluminum salt; ammonium salt; as well as those salts with organic bases such as dialkylamines, e.g., mono or diethylamine, alkanolamines, e.g., ethanolamine, heterocyclic amines, e.g., pyridine, piperidine, piperazine, morpholine and the like may be obtained.

In a still another aspect of this invention, there is provided a pharmaceutical composition which comprises as an active ingredient at least one of a substituted phenylglycolic acid (I) and pharmaceutically acceptable esters and salts thereof. The present composition or preparation may preferably be of the adequate form for oral administration, for example, a tablet, capsule, powder, granule or fine granule form. These dosage forms may be easily prepared according to conventional technique and may comprise commonly employed excipients, binding agents, disintegrators, glidants and other pharmaceutical agents. As the excipient, binding agent and/or disintegrator, there may be, for example, mentioned microcrystalline cellulose, wheat starch, sugar, lactose, gum arabic, tragacanth gum, carboxymethylcellulose and so on. As the glidant, there may be given, e.g., magnesium stearate and talc. Tablets may be also coated according to conventional coating procedures and any commonly employable coating materials such as, for example, shellac, ethylcellulose, hydroxymethylcellulose, polyvinyl pyrrolidone, titanium dioxide and the like may be favourably applied for such purposes.

The present invention also involves a method useful for the treatment of inflammatory diseases and for analgesic and antipyretic purposes which comprises administering an effective amount of a substituted phenylglycolic acid of the formula (I) hereof and pharmaceutically acceptable esters and salts.

This invention will be more fully illustrated by way of the non-limiting Examples and Preparation Examples as given below. In the examples, percents are given on a basis by weight unless otherwise specified.

EXAMPLE 1

Step 1: 2-(2,6-Dichloroanilino)phenylglyoxylic acid

To a solution of 5.8 g of 1-(2,6-dichlorophenyl)indole-2,3-dione (m.p. 174°–175° C.) in 40 ml of ethanol were added 22 ml of a 1 N aqueous sodium hydroxide solution and the resulting mixture was stirred at room temperature for 1 hour. The reaction mixture was concentrated at a bath temperature of not more than 40° C. under a reduced pressure of 5 mmHg. To the residue were added 50 ml of water and the mixture was extracted with 30 ml of ether. The ether extract was separated out. The remaining aqueous layer was acidified with a 5% aqueous hydrochloric acid solution under ice-cooling and the solid thus precipitated was extracted with ether. The ether extract was washed with water and dried over sodium sulfate and concentrated at 10 mmHg without heating. The residue was recrystallized from dichloromethane-hexane to give 6.0 g of 2-(2,6-dichloroanilino)phenylglyoxylic acid as a yellow powder. m.p. 159°–159.5° C. Yield: 97% of theoretical amount

| IR $\nu_{max}^{Nujol}$(cm$^{-1}$): | 3320 (due to NH) |
| --- | --- |
| | 1700 (due to COOH) |
| | 1670 (due to CO) |
| UV$\lambda_{max}^{EtOH}$(m$\mu$): | 377 (due to ) |
| | 256 |
| | 230 |

Step 2: Methyl 2-(2,6-dichloroanilino)phenylglyoxylate

To a solution of 12.4 g of 2-(2,6-dichloroanilino)-phenylglyoxylic acid in 150 ml of anhydrous ether were dropwise added under ice-cooling over 30 minutes 100 ml of a solution of 2 g of diazomethane in anhydrous ehter. After completion of the dropwise addition, stirring was continued under ice-cooling for 1 hour and then at room temperature for further 1 hour. 50 ml of a 0.1 N aqueous hydrochloric acid solution were added to the reaction mixture and the ether layer was separated. The ether layer was then washed with water and dried over anhydrous sodium sulfate. The ether was distilled off at room temperature under a reduced pressure of 10 mmHg and the residue was recrystallized from ethanol to give 12.2 g of methyl 2-(2,6-dichloroanilino) phenylglyoxylate. m.p. 125°–125.5° C. Yield: 94% of theoretical amount

| IR $\nu_{max}^{KBr}$(cm$^{-1}$): | 3250 (NH) |
| --- | --- |
| | 1740 (COOCH$_3$) |
| UV $\lambda_{max}^{EtOH}$(m$\mu$): | 383 () |
| | 258 |

Step 3: Methyl 2-(2,6-dichloroanilino)phenylglycolate

To a solution of 3.24 g of methyl 2-(2,6-dichloroanilino)-phenylglyoxylate in 50 ml of a 0.1 N acetic acid solution in methanol (hereinafter often referred to as "0.1 N acetic acid/methanol") was added 0.6 g of 5% Pt-carbon, and vigorous stirring was effected at room temperature under a hydrogen pressure of 2 atmospheres for 10 hours. The catalyst was filtered off and the filtrate was concentrated at room temperature under a reduced pressure of 10 mmHg. The crystalline substance thus deposited was recovered by filtration and recrystallized from ethanol to give 3.0 g of methyl 2-(2,6-dichloroanilino)phenylglycolate. m.p. 123°–124.5° C.

Yield: 92% of theoretical amount

| IR $\nu_{max}^{KBr}$(cm$^{-1}$): | 3480 (OH) |
| --- | --- |
| | 3360 (NH) |
| | 1740 (COOCH$_3$) |

-continued

UV $\lambda_{max}^{EtOH}$(mμ): 282 (  )

Elementary analysis for $C_{15}H_{13}Cl_2NO_3$(%):

| | C | H | N |
|---|---|---|---|
| Calculated: | 55.23 | 4.02 | 4.29 |
| Found: | 55.19 | 3.96 | 4.38 |

Step 4: 2-(2,6-Dichloroanilino)phenylglycolic acid

To a solution of 13.0 g of methyl 2-(2,6-dichloroanilino)-phenylglycolate in 150 ml of ethanol were added 10 ml of a 5 N aqueous sodium hydroxide solution and the reaction was effected at 80° C. under a nitrogen stream for 1 hour. The ethanol was distilled off under reduced pressure and the residual liquid was diluted with 100 ml of cold water and acidified with a 10% aqueous hydrochloric acid solution. The solid thus deposited was extracted with ether, and the ether extract was washed with water, dried over anhydrous sodium sulfate and then the ether was distilled off at room temperature under reduced pressure. The residue was recrystallized from ether-petroleum ether to give 10.1 g of 2-(2,6-dichloroanilino)phenylglycolic acid. m.p. 140°–142° C. Yield: 81% of theoretical amount.

IR $\nu_{max}^{KBr}$(cm$^{-1}$): 3500 (OH)
3360 (NH)
3320
1695 (COOH)

UV $\lambda_{max}^{EtOH}$(mμ): 280 (  )

Elementary analysis for $C_{14}H_{11}Cl_2NO_3$ (%)

| | C | H | N |
|---|---|---|---|
| Calculated: | 53.87 | 3.55 | 4.49 |
| Found: | 53.57 | 3.71 | 4.57 |

EXAMPLE 2

The same procedures as in Example 1 were repeated except that the Step 2 was effected as mentioned below.

Step 2: Methyl 2-(2,6-dichloroanilino)phenylglyoxylate

To a solution of 12.4 g of 2-(2,6-dichloroanilino)-phenylglyoxylic acid in 80 ml of anhydrous acetone were added 6.05 g of anhydrous potassium carbonate and then 7.5 ml of dimethyl sulfate at room temperature, and the mixture was stirred for 1 hour. The reaction mixture was filtered and washed with anhydrous acetone. The filtrate was concentrated under 10 mmHg without heating. The residue was recrystallized from ethanol to give 12.3 g of methyl 2-(2,6-dichloroanilino)-phenylglyoxylate as yellow prisms. m.p. 124.5-125.5° C. Yield: 95% of theoretical amount IR $\nu_{max}^{KBr}$(cm$^{-1}$): 3250 (NH)
1740 (COOCH₃)

UV $\lambda_{max}^{EtOH}$(mμ): 383 (  )
258

Elementary analysis for $C_{15}H_{11}Cl_2NO_3$ (%)

| | C | H | N |
|---|---|---|---|
| Calculated: | 55.58 | 3.42 | 5.32 |
| Found: | 55.61 | 3.55 | 4.35 |

EXAMPLE 3

The same procedures as in Example 1 were repeated except that the Step 2 was effected as mentioned below.

Step 2: Ethyl 2-(2,6-dichloroanilino)phenylglyoxylate

To a solution of 12.4 g of 2-(2,6-dichloroanilino)-phenylglyoxylic acid in 80 ml of anhydrous acetone were added 6.05 g of anhydrous potassium carbonate and then 8 ml of diethyl sulfate, and the mixture was stirred at room temperature for 1 hour. The reaction mixture was filtered and washed with anhydrous acetone. The filtrate was concentrated under 100 mmHg without heating. The residue was subjected to column chromatography with silica gel (Wacogel C 200), using ether-hexane (1:2) as a developing solvent, to give ethyl 2-(2,6-dichloroanilino)phenylglyoxylate. m.p. 84.0°–85.5° C.

Yield: 96% of theoretical amount

IR $\nu_{max}^{KBr}$(cm$^{-1}$): 3280 (NH)
1740 (COOEt)
1640 (CO)

UV $\lambda_{max}^{EtOH}$(mμ): 383 (  )
258
249

Elementary analysis for $C_{16}H_{13}Cl_2NO_3$ (%):

| | C | H | N |
|---|---|---|---|
| Calculated: | 56.83 | 3.87 | 4.14 |
| Found: | 56.80 | 3.95 | 4.18 |

EXAMPLE 4

The same procedures as in Example 1 were repeated except that the Step 2 was effected as mentioned below.

Step 2: Ethyl 2-(2,6-dichloroanilino)phenylglyoxylate

To a solution of 6.2 g of 2-(2,6-dichloroanilino)-phenylglyoxylic acid in 30 ml of dimethylformamide were added 3.3 g of anhydrous sodium acetate and then dropwise added 3 ml of ethyl bromide under ice-cooling. The mixture was stirred at room temperature for 10 hours. Thereafter, the reaction mixture was poured into 300 ml of water and the whole mixture was extracted with benzene. The benzene extract was washed with water, dried over anhydrous sodium sulfate and then concentrated. The residue was subjected to column chromatography with silica gel (Wacogel C 200), using etherhexane (1:2) as a developing solvent, to give 5.3 g of ethyl 2-(2,6-dichloroanilino)phenylglyoxylate as yellow crystals. m.p. 84°–85° C. Yield: 78% of theoretical amount

| IR $\nu_{max}^{film}$(cm$^{-1}$): | 3280 (NH) |
| | 1740 (COOEt) |
| | 1640 (CO) |

UV $\lambda_{max}^{EtOH}$(m$\mu$): 383 
258
249

Elementary analysis for $C_{16}H_{13}Cl_2NO_3$ (%):

| | C | H | N |
| --- | --- | --- | --- |
| Calculated: | 56.83 | 3.87 | 4.14 |
| Found: | 56.80 | 3.95 | 4.18 |

EXAMPLE 5

The same procedures as in Example 1 were repeated except that the Step 3 was effected as mentioned below.

Step 3: Methyl 2-(2,6-dichloroanilino)phenylglycolate

To a solution of 6.5 g of methyl 2-(2,6-dichloroanilino)phenylglyoxylate in 130 ml of ethanol was added 0.5 g of sodium borohydride while cooling at −15° to −20° C., and the mixture was stirred at 0° C. for 2 hours and then at room temperature for further 1 hour. Thereafter, the reaction mixture was mixed with diluted hydrochloric acid for decomposition, diluted with 500 ml of water and extracted with ether. The ether extract was washed with water, dried over anhydrous sodium sulfate and then concentrated without heating. The resulting residue was recrystallized from ethanol to give 6.2 g of methyl 2-(2,6-dichloroanilino)-phenylglycolate. m.p. 123°–124° C. Yield: 95% of theoretical amount

| IR $\nu_{max}^{KBr}$(cm$^{-1}$): | 3480 (OH) |
| | 3360 (NH) |
| | 1740 (COOCH$_3$) |

UV $\lambda_{max}^{EtOH}$(m$\mu$): 282

Elementary analysis for $C_{15}H_{13}Cl_2NO_3$ (%):

| | C | H | N |
| --- | --- | --- | --- |
| Calculated: | 55.24 | 4.02 | 4.29 |
| Found: | 55.35 | 3.98 | 4.25 |

EXAMPLE 6

The same procedures as in Example 1 were repeated except that the Step 3 was effected as mentioned below.

Step 3: Methyl 2-(2,6-dichloroanilino)phenylglycolate

The same procedures as in the Step 3 of Example 1 were repeated except that 0.1 g of platinum oxide and 50 ml of 1 N acetic acid/ethanol were employed instead of 0.6 g of 5% Pt-carbon and 50 ml of 0.1 N acetic acid/methanol, respectively, thereby yielding 2.8 g of methyl 2-(2,6-dichloroanilino)phenylglycolate. m.p. 123°–124° C. Yield: 85% of theoretical amount

| IR $\nu_{max}^{KBr}$(cm$^{-1}$): | 3480 (OH) |
| | 3360 (NH) |
| | 1740 (COOCH$_3$) |

UV $\lambda_{max}^{EtOH}$(m$\mu$): 282

Elementary analysis for $C_{15}H_{13}Cl_2NO_3$ (%):

| | C | H | N |
| --- | --- | --- | --- |
| Calculated: | 55.23 | 4.02 | 4.27 |
| Found: | 55.29 | 3.86 | 4.30 |

EXAMPLE 7

The same procedures as in Example 1 were repeated except that the Step 3 was effected as mentioned below.

Step 3: Methyl 2-(2,6-dichloroanilino)phenylglycolate

The same procedures as in the Step 3 of Example 1 were repeated except that vigorous stirring was conducted at 50° C. for 3 hours instead of that of at room temperature for 10 hours, thereby yielding 3.0 g of methyl 2-(2,6-dichloroanilino)phenylglycolate. m.p. 123.5°–124.5° C. Yield: 92% of theoretical amount

| IR $\nu_{max}^{KBr}$(cm$^{-1}$): | 3480 (OH) |
| | 3360 (NH) |
| | 1740 (COOCH$_3$) |

UV $\lambda_{max}^{EtOH}$(mμ):  282 (  )

Elementary analysis for $C_{15}H_{13}Cl_2NO_3$ (%):

|  | C | H | N |
|---|---|---|---|
| Calculated: | 55.23 | 4.02 | 4.29 |
| Found: | 55.10 | 3.91 | 4.33 |

EXAMPLE 8

The same procedures as in Example 1 were repeated except that the Step 3 was effected as mentioned below.

Step 3: Methyl 2-(2,6-dichloroanilino)phenylglycolate

The same procedures as in the Step 3 of Example 7 were repeated except that 0.8 g of 5% Pd-BaSO₄ and 50 ml of 0.5 N propionic acid/methanol were employed instead of 0.6 g of 5% Pt-carbon and 50 ml of 0.1 N acetic acid/methanol, respectively, thereby yielding 1.5 g of methyl 2-(2,6-dichloroanilino)phenylglycolate. m.p. 122.5°–123.5° C. Yield: 46% of theoretical amount IR $\nu_{max}^{KBr}$(cm⁻¹):  3480 (OH)
3360 (NH)
1740 (COOCH₃)

UV $\lambda_{max}^{EtOH}$(mμ):  282 (  )

Elementary analysis for $C_{15}H_{13}Cl_2NO_3$ (%):

|  | C | H | N |
|---|---|---|---|
| Calculated: | 55.23 | 4.02 | 4.29 |
| Found: | 55.14 | 3.96 | 4.35 |

EXAMPLE 9

The same procedures as in Example 1 were repeated except that the Step 3 was effected as mentioned below.

Step 3: Ethyl 2-(2,6-dichloroanilino)phenylglycolate

The same procedures as in the Step 3 of Example 5 were repeated except that 6.8 g of ethyl 2-(2,6-dichloroanilino)-phenylglyoxylate were employed instead of 6.5 g of methyl 2-(2,6-dichloroanilino)phenylglyoxylate, thereby yielding 6.2 g of ethyl 2-(2,6-dichloroanilino)phenylglycolate. m.p. 155°–156° C. Yield: 91% of theoretical amount IR $\nu_{max}^{KBr}$(cm⁻¹):  3400 (OH)
3350 (NH)
1735 (COOEt)

UV $\lambda_{max}^{EtOH}$(mμ):  282 (  )

Elementary analysis for $C_{16}H_{15}Cl_2NO_3$ (%):

|  | C | H | N |
|---|---|---|---|
| Calculated: | 56.49 | 4.44 | 4.12 |
| Found: | 56.52 | 4.38 | 4.10 |

EXAMPLE 10

The same procedures as in Example 1 were repeated except that the Step 3 was effected as mentioned below.

Step 3: Ethyl 2-(2,6-dichloroanilino)phenylglycolate

The same procedures as in the Step 3 of Example 9 were repeated except that 100 ml of tetrahydrofuran and 15 g of lithium tri-tert-butoxy aluminum hydride were employed instead of 130 ml of ethanol and 0.5 g of sodium borohydride, respectively, thereby yielding 5.3 g of ethyl 2-(2,6-dichloroanilino)phenylglycolate. m.p. 155°–156° C. Yield: 82% of theoretical amount IR $\nu_{max}^{KBr}$(cm⁻¹):  3400 (OH)
3350 (NH)
1735 (COOEt)

UV $\lambda_{max}^{EtOH}$(mμ):  282 (  )

Elementary analysis for $C_{16}H_{15}Cl_2NO_3$ (%):

|  | C | H | N |
|---|---|---|---|
| Calculated: | 56.49 | 4.44 | 4.12 |
| Found: | 56.43 | 4.21 | 4.01 |

EXAMPLE 11

The same procedures as in Example 1 were repeated except that the Step 3 was effected as mentioned below.

Step 3: Ethyl 2-(2,6-dichloroanilino)phenylglycolate

The same procedures as in the Step 3 of Example 1 were repeated except that 3.42 g of ethyl 2-(2,6-dichloroanilino)-phenylglyoxylate were employed instead of 3.24 g of methyl 2-(2,6-dichloroanilino)phenylglyoxylate, thereby yielding 2.9 g of ethyl 2-(2,6-dichloroanilino)phenylglycolate m.p. 154.5°–156.0° C. Yield: 86% of theoretical amount IR $\nu_{max}^{KBr}$(cm⁻¹):  3400 (OH)
3350 (NH)
1735 (COOEt)

UV $\lambda_{max}^{EtOH}$(mμ): 282 (  )

Elementary analysis for $C_{16}H_{15}Cl_2NO_3$ (%):

| | C | H | N |
|---|---|---|---|
| Calculated: | 56.49 | 4.44 | 4.12 |
| Found: | 56.58 | 4.50 | 4.21 |

EXAMPLE 12

The same procedures as in Example 1 were repeated except that the Step 3 was effected as mentioned above.

Step 3: Ethyl 2-(2,6-dichloroanilino)phenylglycolate

The same procedures as in the Step 3 of Example 6 were repeated except that 3.38 g of ethyl 2-(2,6-dichloroanilino)-phenylglyoxylate were employed instead of 3.24 g of methyl 2-(2,6-dichloroanilino)phenylglyoxylate, thereby yielding 3.2 g of ethyl 2-(2,6-dichloroanilino)phenylglycolate. m.p. 154°–155.5° C. Yield: 93% of theoretical amount IR $\nu_{max}^{KBr}$(cm$^{-1}$): 3400 (OH)
3350 (NH)
1735 (COOEt)

UV $\lambda_{max}^{EtOH}$(mμ): 282 (  )

Elementary analysis for $C_{16}H_{15}Cl_2NO_3$ (%):

| | C | H | N |
|---|---|---|---|
| Calculated: | 56.49 | 4.44 | 4.12 |
| Found: | 56.50 | 4.31 | 4.03 |

EXAMPLE 13

The same procedures as in Example 1 were repeated except that the Step 3 was effected as mentioned below.

Step 3: Ethyl 2-(2,6-dichloroanilino)phenylglycolate

The same procedures as in the Step 3 of Example 8 were repeated except that 0.23 g of platinum black and 3.38 g of methyl 2-(2,6-dichloroanilino)phenylglyoxylate were employed instead of 0.8 g of 5% Pd-BaSO$_4$ and 3.24 g of the methyl ester, respectively, thereby yielding 2.6 g of ethyl 2-(2,6-dichloroanilino)phenylglycolate. m.p. 154.5°–155.5° C. Yield: 78% of theoretical amount IR $\nu_{max}^{KBr}$(cm$^{-1}$): 3400 (OH)
3350 (NH)
1735 (COOEt)

UV $\lambda_{max}^{EtOH}$(mμ): 282 (  )

Elementary analysis for $C_{16}H_{15}Cl_2NO_3$ (%):

| | C | H | N |
|---|---|---|---|
| Calculated: | 56.49 | 4.44 | 4.12 |
| Found: | 56.31 | 4.50 | 4.25 |

EXAMPLE 14

The same procedures as in Example 1 were repeated except that the Step 4 was effected as mentioned below.

Step 4: 2-(2,6-Dichloroanilino)phenylglycolic acid

The same procedures as in the Step 4 of Example 1 were repeated except that 13.6 g of ethyl 2-(2,6-dichloroanilino)-phenylglycolate were employed instead of 13.0 g of methyl 2-(2,6-dichloroanilino)phenylglycolate, thereby yielding 9.7 g of 2-(2,6-dichloroanilino)phenylglycolic acid. m.p. 139°–141.5° C. Yield: 78% of theoretical amount IR $\nu_{max}^{KBr}$(cm$^{-1}$): 3500 (OH)
3360 (NH)
3320
1695 (COOH)

UV $\lambda_{max}^{EtOH}$(mμ): 280 (  )

Elementary analysis for $C_{14}H_{11}Cl_2NO_3$ (%):

| | C | H | N |
|---|---|---|---|
| Calculated: | 53.87 | 3.55 | 4.49 |
| Found: | 53.73 | 3.65 | 4.38 |

EXAMPLE 15

The same procedures as in Example 1 were repeated except that the Step 4 was effected as mentioned below.

Step 4: 2-(2,6-Dichloroanilino)phenylglycolic acid

The same procedures as in the Step 4 of Example 14 were repeated except that 12 ml of a 5 N aqueous potassium carbonate solution was employed instead of 10 ml of a 5 N aqueous sodium hydroxide solution, thereby yielding 9.8 g of 2-(2,6-dichloroanilino)phenylglycolic acid. m.p. 139°–140° C. Yield: 79% of theoretical amount.

IR $\nu_{max}^{KBr}$(cm$^{-1}$): 3500 (OH)

```
                          3360 (NH)
                          3320
                          1695 (COOH)
```

UV $\lambda_{max}^{EtOH}$(mμ):  280 (  )

Elementary analysis for $C_{14}H_{11}Cl_2NO_3$ (%):

|              | C     | H    | N    |
|--------------|-------|------|------|
| Calculated:  | 53.87 | 3.55 | 4.49 |
| Found:       | 53.69 | 3.58 | 4.60 |

EXAMPLE 16

Sodium 2-(2,6-dichloroanilino)phenylglycolate

To a solution of 6.24 g of 2-(2,6-dichloroanilino)-phenylglycolic acid in 30 ml of ethanol were added 10 ml of a 5 N aqueous sodium hydroxide solution and the mixture was stirred at room temperature for 1 hour. Then, 20 ml of water were added, and the mixture was concentrated to have a volume of 30 ml. The concentrate was cooled and the solid thus deposited was recovered by filtration. Recrystallization from water gave sodium 2-(2,6-dichloroanilino)phenylglycolate. m.p. 101°–104° C.

IR$\nu_{max}^{KBr}$ (cm$^{-1}$): 1620, 1510 (COO$^-$)

The pharmaceutical preparations of this invention will be more fully illustrated by way of the following Preparation Examples.

PREPARATION EXAMPLE 1

Tablets were prepared with the following ingredients according to the item 14 "Tablets" prescribed in the Japanese Pharmacopoeia (J.P.). Each tablet contains 50 mg of the active ingredient.

| Ingredient | Content/Tab. (mg) |
|---|---|
| 1. Sodium 2-(2,6-dichloroanilino)-phenylglycolate | 50 |
| 2. Avicel (registered trade mark of microcrystalline cellulose manufactured and sold by Asahi Kasei Kogyo K.K., Japan) | 50 |
| 3. Lactose | 80 |
| 4. Wheat starch | 40 |
| 5. Polyvinyl acetate | 2 |
| 6. Magnesium stearate | 2 |

PREPARATION EXAMPLE 2

Tablets as prepared in the above Preparation Example 1 were coated with a syrup which was prepared from shellac, gum arabic, silicon dioxide, talc and sugar (of the formulation of 1:3:1:10:30) together with a minor amount of pigments, thereby producing sugar-coated tablets.

PREPARATION EXAMPLE 3

Tablets as prepared in the above Preparation Example 1 were coated with a composition of shellac, hydroxymethyl cellulose, titanium dioxide, polyvinyl pyrrolidone and pigments, thereby producing coated tablets.

What is claimed is:

1. A compound of the formula:

and its pharmaceutically acceptable salts with an inorganic or organic base and pharmaceutically acceptable lower alkyl esters.

2. A pharmaceutically acceptable salt according to claim 1, wherein said inorganic base is a member selected from the group consisting of sodium hydroxide and potassium hydroxide.

3. A pharmaceutically acceptable lower alkyl ester according to claim 1, wherein said lower alkyl is a member selected from the group consisting of methyl and ethyl.

4. A pharmaceutical composition comprising an effective amount of a compound according to claim 1 and a pharmaceutically acceptable carrier therefor.

5. A pharmaceutical composition comprising an effective amount of a pharmaceutically acceptable salt according to claim 2 and a pharmaceutically acceptable carrier therefor.

6. A pharmaceutical composition comprising an effective amount of a pharmaceutically acceptable ester according to claim 3 and a pharmaceutically acceptable carrier therefor.

7. A method of reducing inflammation which comprises administering to a patient an effective amount of a compound according to claim 1.

8. A method of reducing inflammation which comprises administering to a patient an effective amount of a compound according to claim 2.

9. A method of reducing inflammation which comprises administering to a patient an effective amount of a compound according to claim 3.